United States Patent
Yamasaki

(10) Patent No.: US 11,141,387 B2
(45) Date of Patent: Oct. 12, 2021

(54) MEMANTINE-CONTAINING TRANSDERMALLY ABSORBABLE LIQUID

(71) Applicant: MEDRX CO., LTD., Higashikagawa (JP)

(72) Inventor: Keiko Yamasaki, Kagawa (JP)

(73) Assignee: MEDRX CO., LTD., Kagawa (JP)

(*) Notice: Subject to any disclaimer, the term of this patent is extended or adjusted under 35 U.S.C. 154(b) by 12 days.

(21) Appl. No.: 16/604,535

(22) PCT Filed: Apr. 10, 2018

(86) PCT No.: PCT/JP2018/014984
§ 371 (c)(1),
(2) Date: Oct. 10, 2019

(87) PCT Pub. No.: WO2018/190313
PCT Pub. Date: Oct. 18, 2018

(65) Prior Publication Data
US 2020/0179309 A1   Jun. 11, 2020

(30) Foreign Application Priority Data

Jan. 5, 2017 (JP) .............. JP2017-090921
Apr. 11, 2017 (JP) .............. JP2017-078559
Jun. 6, 2017 (JP) .............. JP2017-111885

(51) Int. Cl.
| | |
|---|---|
| A61K 31/13 | (2006.01) |
| A61K 9/00 | (2006.01) |
| A61K 47/24 | (2006.01) |
| A61K 47/10 | (2017.01) |
| A61K 47/18 | (2017.01) |

(52) U.S. Cl.
CPC ............ A61K 31/13 (2013.01); A61K 9/0014 (2013.01); A61K 47/10 (2013.01); A61K 47/18 (2013.01); A61K 47/24 (2013.01)

(58) Field of Classification Search
CPC ...... A61K 31/13; A61K 9/0014; A61K 47/10; A61K 47/18; A61K 47/24

USPC .......................................................... 514/740
See application file for complete search history.

(56) References Cited

U.S. PATENT DOCUMENTS

| | | |
|---|---|---|
| 2012/0149664 A1 | 6/2012 | Yamasaki et al. |
| 2016/0256552 A1 | 9/2016 | Yamasaki |
| 2018/0147138 A1 | 5/2018 | Yamasaki |

FOREIGN PATENT DOCUMENTS

| | | |
|---|---|---|
| EP | 3 069 712 | 11/2014 |
| JP | 10-194994 | 7/1998 |
| JP | 2009-013171 | 1/2009 |
| JP | 2009-524586 | 7/2009 |
| WO | WO 2007/070679 | 6/2007 |
| WO | WO 2011/024354 | 3/2011 |
| WO | WO 2015/072564 | 5/2015 |
| WO | WO 2016/186157 | 11/2016 |

OTHER PUBLICATIONS

International Search Report, Application No. PCT/JP2018/014984, dated Jun. 5, 2018, in 3 pages.

*Primary Examiner* — Kristin A Vajda
(74) *Attorney, Agent, or Firm* — Morgan, Lewis & Bockius LLP

(57) ABSTRACT

An external preparation containing memantine which has less skin irritation and excellent skin permeability, and also, which is suitable for continuous administration for a long period of time. The external preparation contains memantine or a salt thereof, and further contains 0.05 to 1.5% by weight of phosphatidylcholine, 35 to 55% by weight of propylene glycol, 18 to 30% by weight of glycerine, and 22 to 32% by weight of water. The content of water less than 22% by weight may increase skin irritation, and the content of water more than 32% by weight may decrease skin permeability. The content of glycerin less than 18% by weight may increase skin irritation, and the content of glycerin more than 30% by weight may decrease skin permeability.

20 Claims, 1 Drawing Sheet

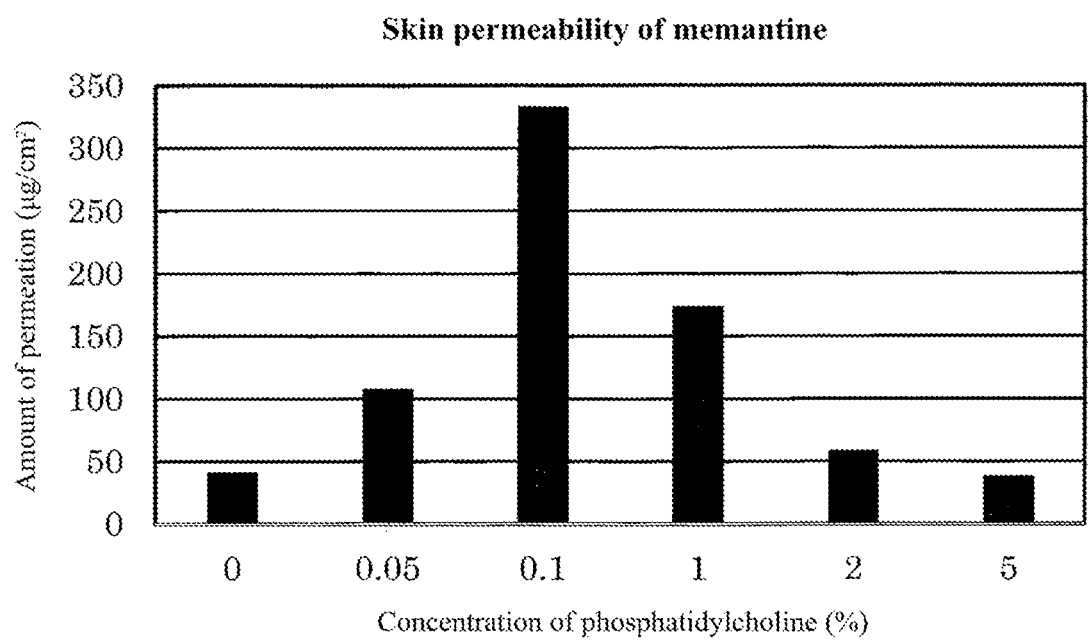

MEMANTINE-CONTAINING TRANSDERMALLY ABSORBABLE LIQUID

FIELD OF THE INVENTION

The present invention relates to a transdermal absorptive liquid formulation containing memantine as an active ingredient, and more particularly to a composition for external use in which skin irritation is reduced.

Description of the Related Art

Memantine has an N-methyl-D-aspartate (NMDA) receptor inhibitory effect and is used as an agent for the treatment of dementia of Alzheimer's type. Currently, film-coated tablets and orally disintegrating tablets, which are oral dosage forms of memantine hydrochloride, are available. Meanwhile, the progress of dementia may make ingestion of a therapeutic agent difficult. Thus, transdermal administration of memantine by patch formulation has been proposed. However, transdermal administration of memantine is not suitable for long-term continuous administration because of its strong skin irritation.

As a means for solving the problem of skin irritation of memantine, there have been proposed a method for setting the skin permeation rate of memantine to a constant value or less (Patent Document 1), a method for reducing skin irritation by a composition containing phosphatidylcholine (Patent Document 2), and the like.

PRIOR ART LITERATURES

Patent Literatures

Patent Document 1: JP-A-2009-13171
Patent Document 2: WO 2016/186157

SUMMARY OF THE INVENTION

Problem to be Solved by the Invention

An object of the present invention is to provide an external preparation containing memantine, which has less skin irritation and excellent skin permeability, and also, which is suitable for continuous administration for a long period of time.

Means for Solving the Problem

As a result of intensive investigation, the present inventor has found that the above problem can be solved by a composition containing phosphatidylcholine, propylene glycol, glycerin, and water in a constant ratio in a transdermal absorptive liquid formulation of memantine, and has completed the present invention.

Examples of the present invention can include the below-mentioned [1] to [8].
[1] A transdermal absorptive liquid formulation, comprising memantine or a salt thereof, and further comprising:
(a) 0.05 to 1.5% by weight of phosphatidylcholine,
(b) 35 to 55% by weight of propylene glycol,
(c) 18 to 30% by weight glycerin, and
(d) 22 to 32% by weight of water.
[2] The transdermal absorptive liquid formulation according to the above [1], further comprising an alkanolamine and/or a higher alcohol.
[3] The transdermal absorptive liquid formulation according to the above [2], wherein the alkanolamine is triethanolamine.
[4] The transdermal absorptive liquid formulation according to the above [2] or [3], wherein the higher alcohol is oleyl alcohol.
[5] A transdermal absorption promoting agent for a transdermal absorptive liquid formulation, comprising memantine or a salt thereof as an active ingredient, and further comprising:
(a) 0.05 to 1.5% by weight of phosphatidylcholine,
(b) 35 to 55% by weight of propylene glycol,
(c) 18 to 30% by weight glycerin, and
(d) 22 to 32% by weight of water,
wherein skin irritation is reduced.
[6] The transdermal absorption promoting agent according to the above [5], further comprising an alkanolamine and/or a higher alcohol.
[7] The transdermal absorption promoting agent according to the above [6], wherein the alkanolamine is triethanolamine.
[8] The transdermal absorption promoting agent according to the above [6] or [7], wherein the higher alcohol is oleyl alcohol.

BRIEF DESCRIPTION OF THE DRAWINGS

FIG. 1 is a graph showing changes in an amount of skin permeation of memantine as depending on changes in phosphatidylcholine concentration.

DETAILED DESCRIPTION OF THE PREFERRED EMBODIMENT

The transdermal absorptive liquid formulation of the present invention (hereinafter referred to as the "liquid formulation of the present invention") contains memantine (1-amino-3,5-dimethyladamantane) or a salt thereof (hereinafter also together simply referred to as "memantine") as an active ingredient. Examples of the salt of memantine can include inorganic acid salts such as hydrochloride, hydrobromide, nitrate, sulfate, and phosphate; and organic acid salts such as propionate, lactate, tartrate, oxalate, fumarate, maleate, citrate, and malonate. Among them, memantine hydrochloride is generally used. Memantine or a salt thereof may be contained in the range of, for example, 0.1 to 25% by weight, 1 to 15% by weight, or 4 to 12% by weight, based on the total weight of the liquid formulation of the present invention.

Memantine or a salt thereof is dissolved or colloidally dispersed in an aqueous solvent consisting of phosphatidylcholine, propylene glycol, glycerin, and water.

Phosphatidylcholine is a generic term for the compounds of Formula (I) and is usually provided as differing mixtures of $R^1$ and $R^2$ types and combinations.

[Chemical Formula 1]

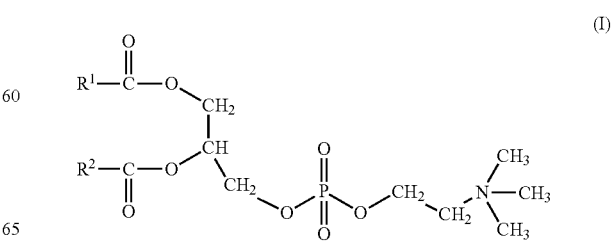

(In the formula, $R^1$ and $R^2$ are the same or different, and each represents $C_{12-22}$ hydrocarbon group.)

In the present invention, unsaturated phosphatidylcholine can be used in which at least one of $R^1$ and $R^2$ is an unsaturated hydrocarbon group. Although saturated hydrocarbon groups such as palmityl groups (16:0), stearyl groups (18:0) and the like may be included as $R^1$ and $R^2$, unsaturated phosphatidylcholines which can be used herein have a content of such saturated hydrocarbon groups of less than 80%, preferably less than 70%, more preferably less than 60%, and particularly preferably less than 50%. Examples of the unsaturated hydrocarbon group include a palmitoyl group (16:1), an oleyl group (18:1), a linoleyl group (18:2), and a linolenyl group (18:3). In the present invention, the unsaturated phosphatidylcholine preferably has a content of an unsaturated hydrocarbon group having 18 carbon atoms, such as an oleyl group, a linoleyl group, or a linolenyl group, of 20% or more, more preferably 30% or more, and particularly preferably 40% or more. The use of unsaturated phosphatidylcholine makes it possible to prepare stable solutions or colloidal dispersions with excellent skin permeability.

In the present invention, as the unsaturated phosphatidylcholine, phosphatidylcholine of high purity, which is naturally derived such as soybean lecithin and egg yolk lecithin and has a phosphatidylcholine content of 95% or more, can be preferably used. It is not preferable to use hydrogenated phosphatidylcholine subjected to hydrogenation treatment or phosphatidylcholine which is chemically and/or biologically modified, such as lysophosphatidylcholine obtained by enzyme treatment or the like, because it may not provide a stable colloidal dispersion. However, even phosphatidylcholines that have been chemically and/or biologically modified, such as partial hydrogenates of naturally occurring lecithins, high purity phosphatidylcholines with a high degree of unsaturation (e.g., phosphatidylcholines having an iodine value of 20 or greater and a lysolecithin content of less than 10%) can be used as the "unsaturated phosphatidylcholines" of the present invention.

The content of phosphatidylcholine is usually selected from 0.01 to 2% by weight, based on the total weight of the liquid formulation of the present invention. The skin permeation rate of memantine is closely dependent on the concentration of phosphatidylcholine. The content of phosphatidylcholine is preferably in the range of 0.05 to 1.5% by weight, more preferably in the range of 0.075 to 1.0% by weight. Especially in the range of 0.09 to 0.11% by weight, the skin permeability of memantine is remarkably improved.

The content of water, e.g., purified water, ranges from about 22% to about 32% by weight, based on the total weight of the liquid formulation of the present invention. The content of water less than about 22% by weight may increase skin irritation, and the content of water more than about 32% by weight may decrease skin permeability.

The content of glycerin ranges from about 18% to about 30% by weight, based on the total weight of the liquid formulation of the present invention. The content of glycerin less than about 18% by weight may increase skin irritation, and the content of glycerin more than about 30% by weight may decrease skin permeability.

The weight ratio of water to glycerin may be, for example, water:glycerin=0.9:1 to 1.5:1, preferably water:glycerin=1: 0.9 to 1.4:1.

The content of propylene glycol may range from about 35% to about 55% by weight, preferably from about 40% to about 50% by weight, based on the total weight of the liquid formulation of the present invention. The content of propylene glycol less than about 35% by weight may make skin permeability less, and the content of propylene glycol more than about 55% by weight may make skin irritation strong.

The weight ratio of water to propylene glycol can be, for example, water:propylene glycol=1:1.2 to 1:2.1, water:propylene glycol=1:1.5 to 1:2.0.

The weight ratio of glycerin to propylene glycol can be, for example, glycerin:propylene glycol=1:1.4 to 1:2.6, glycerin:propylene glycol=1:1.6 to 1:2.4.

The liquid formulation of the present invention preferably further contains an alkanolamine. The inclusion of the alkanolamine further enhances the skin permeability of memantine. As the alkanolamine, a primary, secondary or tertiary alkanolamine having 2 to 12 carbon atoms can be used. Among them, secondary or tertiary alkanolamines are preferable, and tertiary alkanolamines are particularly preferable. Specific examples include diethanolamine, triethanolamine, diisopropanolamine, and triisopropanolamine. Triethanolamine is particularly preferred because of its excellent skin permeation promoting effect. The content of the alkanolamine can be selected from the range of about 0.001% to about 0.1% by weight of the total weight of the liquid formulation of the present invention.

The liquid formulation of the present invention may further contain a higher alcohol such as oleyl alcohol and isostearyl alcohol. The inclusion of the higher alcohol can further improve the skin permeability of memantine. In particular, the delay time of transdermal absorption of memantine is shortened and the maximum skin permeation rate can be reached quickly after application to the skin. The content of the higher alcohol can be selected from the range of about 0.01% to about 2.0% by weight, preferably from about 0.01 to about 1.0% by weight, or from about 0.04 to about 0.06% by weight, based on the total weight of the liquid formulation of the present invention.

The liquid formulation of the present invention may further contain various additives used in external preparations or cosmetics as necessary. Such additives include perfumes, antioxidants, preservatives, pigments, buffers, pH adjusters, ultraviolet absorbers, antimicrobial agents, and the like. Examples of the antioxidant include tocopherol acetate, sodium edetate, erythorbic acid, 1,3-butylene glycol, and sodium pyrosulfite. Examples of the preservative include sorbic acid, taurine, and the like. Examples of the pH adjuster include organic acids such as citric acid, acetic acid, and tartaric acid; inorganic acids such as phosphoric acid and hydrochloric acid; and phosphates such as sodium hydrogen phosphate and dipotassium phosphate.

The method of applying the liquid formulation of the present invention to the skin is not particularly limited, and examples thereof include a method of applying or spraying the liquid formulation of the present invention, a method of applying an appropriate carrier on which the liquid formulation of the present invention is carried, and the like. Among them, a method of attaching a carrier (nonwoven fabric, foamed matrix, or the like) carrying the liquid formulation of the present invention is preferable from the viewpoint of easiness of dose adjustment and handling.

EXAMPLES

In the following, the present invention will be explained in more detail by way of examples, which do not limit the mode for carrying out the present invention in any way.

[Skin Permeability Test]

Liquid formulations A to G were prepared in the compositions (weight %) shown in Table 1. The obtained liquid formulation was subjected to an in vitro skin permeability test using Franz Cell. The skin used in the study was 5-week-old hairless rat (male) abdomen excised skin. JP (The Japanese Pharmacopoeia) glycerin in the table contains about 15% by weight of water. The cumulative skin permeation (μg/cm$^2$) for 6 hours after initiation of the study is shown in Table 1.

[Skin Irritation Test]

The resulting liquid formulation was impregnated into a nonwoven fabric and applied to the surface of mammalian skin for 24 hours to evaluate skin irritation. The results are given in Table 1. The evaluation of irritation was visually confirmed, and the following criteria were used.

++: Obvious erythema was observed
+: Erythema was observed.
−: No skin irritation

TABLE 1

|  | A | B | C | D | E | F | G |
|---|---|---|---|---|---|---|---|
| Memantine Hydrochloride | 5.0 | 5.0 | 5.0 | 5.0 | 5.0 | 6.0 | 10.0 |
| Phosphatidylcholine | 0.1 | 0.1 | 0.1 | 0.1 | 0.1 | 0.5 | 0.1 |
| Propylene Glycol | 42.28 | 27.38 | 30.18 | 47.38 | 57.78 | 72.78 | 37.84 |
| JP glycerin | 39.2 | 29.4 | 29.4 | 23.7 | 13.3 |  | 26.0 |
| Purified Water | 13.3 | 38 | 35.1 | 23.7 | 23.7 | 5.5 | 26.0 |
| 1,3-butanediol |  |  |  |  |  | 15 |  |
| Higher alcohol | 0.1 | 0.1 | 0.2 | 0.1 | 0.1 | 0.2 | 0.05 |
| Triethanolamine | 0.02 | 0.02 | 0.02 | 0.02 | 0.02 | 0.02 | 0.01 |
| Total | 100 | 100 | 100 | 100 | 100 | 100 | 100.0 |
| Skin irritation | + | − | − | − | + | ++ | − |
| Cumulative skin permeation (μg/cm$^2$) | 151 | 76.1 | 83.3 | 882.6 | 955.3 | 618.6 | 1979.1 |

Liquid formulations D and G had excellent skin permeability and no skin irritation. Liquid formulations B and C had no skin irritation, but whereas memantine permeation through the skin was insufficient. This is considered to be attributable to the fact that the content of water is high and the content of propylene glycol is low. Liquid formulation E was excellent in the skin permeability of memantine, but skin irritation was observed. This is considered to be attributable to the high content of propylene glycol and the low content of glycerin. Liquid formulation A was low in skin permeability, and caused skin irritation. This is considered to be attributable to the fact that the content of glycerin is high and the content of water is low. Liquid formulation F had excellent skin permeability by containing propylene glycol and phosphatidylcholine, but obvious skin irritation (erythema) was observed. This is thought to be due to the absence of glycerin.

[In Vitro Skin Permeability Test with Pig Skin/Rabbit Skin Primary Irritation Test]

Liquid formulations of Examples 1 and 2 and Comparative Example 1 were prepared in the compositions shown in Table 2. The obtained liquid formulations were subjected to an in vitro skin permeability test using pig skin and a rabbit skin primary irritation test. The cumulative skin permeation (m/cm$^2$) at the respective sampling points is shown in Table 2.

In the primary skin irritation test, a nonwoven fabric (2.5 cm×2.5 cm) impregnated with a liquid formulation was applied to the back of rabbits for 24 hours, and the skin irritation after peeling was evaluated by the Draize test. Primary irritation index (P.I.I.) is shown in Table 2.

TABLE 2

|  |  | Example 1 | Example 2 | Comparative Example 1 |
|---|---|---|---|---|
| Memantine Hydrochloride |  | 5.0 | 5.0 | 6.0 |
| Phosphatidylcholine |  | 0.1 | 0.2 | 0.5 |
| Propylene Glycol |  | 46.7 | 46.6 | 77.1 |
| JP glycerin |  | 24.0 | 24.0 | 0.0 |
| Purified Water |  | 24.0 | 24.0 |  |
| Triethanolamine |  | 0.014 | 0.014 | 0.250 |
| Oleyl alcohol |  | 0.15 | 0.15 | 0.8 |
| 1,3-butanediol |  |  |  | 15.3 |
| Total |  | 100.0 | 100.0 | 100.0 |
| Cumulative skin permeation | 3 hr | 2.39 |  | 0 |
|  | 5 hr | 9.92 |  | 1.35 |
| (μg/cm$^2$) | 7 hr | 21.55 |  | 6.11 |
|  | 22 hr | 310.91 |  | 344.87 |
|  | 24 hr | 354.47 |  | 426.99 |
| P.I.I |  | 0.1 | 0.1 | 1.5 |

In the liquid formulation of the present invention of the example, a sufficient skin permeability of memantine was obtained, and whereas skin irritation was hardly observed.

Six liquid formulations with different phosphatidylcholine concentrations (Ex. 3-1 to Ex. 3-3 and Comparative Ex. 3-1 to 3-3) were prepared in the composition (weight %) shown in Table 3, and the skin permeation of memantine was measured using Franz Cell.

The skin used in the study was 5-week-old hairless rat (male) abdomen excised skin. The cumulative skin permeation (m/cm$^2$) for 6 hours after initiation of the test is shown in Table 3 and FIG. 1.

TABLE 3

|  | Comparative Ex. 3-1 | Ex. 3-1 | Ex. 3-2 | Ex. 3-3 | Comparative Ex. 3-2 | Comparative Ex. 3-3 |
|---|---|---|---|---|---|---|
| Memantine Hydrochloride | 5.0 | 5.0 | 5.0 | 5.0 | 5.0 | 5.0 |
| Phosphatidylcholine | 0.0 | 0.05 | 0.10 | 1.00 | 2.00 | 5.00 |
| Propylene | 40.986 | 40.936 | 40.886 | 39.986 | 38.986 | 35.986 |

TABLE 3-continued

|  | Comparative Ex. 3-1 | Ex. 3-1 | Ex. 3-2 | Ex. 3-3 | Comparative Ex. 3-2 | Comparative Ex. 3-3 |
|---|---|---|---|---|---|---|
| Glycol | | | | | | |
| JP glycerin | 27.0 | 27.0 | 27.0 | 27.0 | 27.0 | 27.0 |
| Purified Water | 27.0 | 27.0 | 27.0 | 27.0 | 27.0 | 27.0 |
| Triethanolamine | 0.014 | 0.014 | 0.014 | 0.014 | 0.014 | 0.014 |
| Total | 100 | 100 | 100 | 100 | 100 | 100 |
| Cumulative skin permeation ($\mu g/cm^2$) | 40.6 | 107.3 | 332.8 | 173.5 | 57.9 | 37.7 |

The skin permeation of memantine was greatest in Example 3-2, wherein the phosphatidylcholine concentration was 0.1% by weight. That shows a large dependence on the phosphatidylcholine concentration.

Examples 4 to 6

Liquid formulations of Examples 4 to 6 were prepared in the usual manner with the composition (weight %) shown in Table 4.

TABLE 4

|  | Example 4 | Example 5 | Example 6 |
|---|---|---|---|
| Memantine Hydrochloride | 5.0 | 7.5 | 10.0 |
| Phosphatidylcholine | 0.1 | 0.1 | 0.1 |
| Propylene Glycol | 46.149 | 43.644 | 45.139 |
| Concentrated Glycerin | 24.0 | 24.0 | 19.0 |
| Purified Water | 24.0 | 24.0 | 25.0 |
| Triethanolamine | 0.01 | 0.015 | 0.020 |
| Oleyl alcohol | 0.05 | 0.05 | 0.05 |
| Sodium Hydrogen Phosphate Hydrate | 0.501 | 0.501 | 0.501 |
| Dipotassium phosphate | 0.190 | 0.190 | 0.190 |
| Total | 100.0 | 100.0 | 100.0 |

In the liquid formulations of Examples 4 to 6, a sufficient skin permeability of memantine was obtained, and whereas skin irritation was hardly observed.

What is claimed is:

1. A transdermal absorptive liquid formulation, comprising memantine or a salt thereof, and further comprising:
    (a) 0.05 to 1.5% by weight of phosphatidylcholine,
    (b) 35 to 55% by weight of propylene glycol,
    (c) 18 to 30% by weight glycerin, and
    (d) 22 to 32% weight of water,
    wherein the only active ingredient included in the transdermal absorptive liquid formulation is memantine or a salt thereof.

2. The transdermal absorptive liquid formulation according to claim 1, further comprising an alkanolamine.

3. The transdermal absorptive liquid formulation according to claim 1, wherein the transdermal absorptive liquid formulation further comprises a higher alcohol.

4. The transdermal absorptive liquid formulation according to claim 1, wherein a weight ratio of water to glycerin is from 0.9:1 to 1.5:1.

5. The transdermal absorptive liquid formulation according to claim 1, wherein a weight ratio of glycerin:propylene glycol is 1:1.4 to 1:2.6.

6. The transdermal absorptive liquid formulation according to claim 2, wherein the alkanolamine comprises triethanolamine.

7. The transdermal absorptive liquid formulation according to claim 3, wherein the higher alcohol comprises oleyl alcohol.

8. The transdermal absorptive liquid formulation according to claim 1, wherein primary irritation index of the formulation is 0.1.

9. The transdermal absorptive liquid formulation according to claim 3, wherein a content of the higher alcohol is in a range of 0.01% to 2.0% by weight based on a total weight of the transdermal absorptive liquid formulation.

10. The transdermal absorptive liquid formulation according to claim 1, the transdermal absorptive liquid formulation further comprises a pH adjuster.

11. A method of treating dementia of Alzheimer's type in a subject, the method comprising administering to the subject a therapeutically effective amount of a transdermal absorptive liquid formulation comprising memantine or a salt thereof, and further comprising:
    (a) 0.05 to 1.5% by weight of phosphatidylcholine,
    (b) 35 to 55% by weight of propylene glycol,
    (c) 18 to 30% by weight glycerin, and
    (d) 22 to 32% weight of water.

12. The method according to claim 11, further comprising an alkanolamine.

13. The method according to claim 11, wherein the transdermal absorptive liquid formulation further comprises a higher alcohol.

14. The method according to claim 11, wherein a weight ratio of water to glycerin is from 0.9:1 to 1.5:1.

15. The method according to claim 11, wherein a weight ratio of glycerin to propylene glycol is 1:1.4 to 1:2.6.

16. The method according to claim 12, wherein the alkanolamine comprises triethanolamine.

17. The method according to claim 13, wherein the higher alcohol comprises oleyl alcohol.

18. The method according to claim 11, wherein primary irritation index of the formulation is 0.1.

19. The method according to claim 13, wherein a content of the higher alcohol is in a range of 0.01% to 2.0% by weight based on a total weight of the transdermal absorptive liquid formulation.

20. The method according to claim 11, the transdermal absorptive liquid formulation further comprises a pH adjuster.

* * * * *